United States Patent [19]

Pennington

[11] Patent Number: 5,033,850
[45] Date of Patent: Jul. 23, 1991

[54] GAS FLOW CHAMBER FOR USE IN ATOMIC ABSORPTION AND PLASMA SPECTROSCOPY

[76] Inventor: Hurm D. Pennington, Rte. 2, Box 361, Bryan, Tex. 77803

[21] Appl. No.: 500,367

[22] Filed: Mar. 28, 1990

[51] Int. Cl.⁵ .................................................. G01J 3/30
[52] U.S. Cl. .................................. 356/315; 356/417; 431/126; 431/346
[58] Field of Search ............... 356/300, 311, 315, 316, 356/326, 417; 431/4, 126; 239/422, 424, 425

[56] References Cited

U.S. PATENT DOCUMENTS

| | | | |
|---|---|---|---|
| 2,517,666 | 8/1950 | Hood | 356/315 |
| 2,769,366 | 11/1956 | Honma | 356/315 |
| 3,592,608 | 10/1968 | White | 356/417 |
| 4,220,413 | 9/1980 | Targowski et al. | 356/315 |
| 4,367,042 | 1/1983 | Smith, Jr. et al. | 356/315 |

*Primary Examiner*—Richard A. Rosenberger
*Assistant Examiner*—Hoa Q. Pham
*Attorney, Agent, or Firm*—Arnold, White & Durkee

[57] ABSTRACT

The present invention is directed to atomic absorption and plasma spectometer of the type that senses a special characteristic of a flame of absorption or emission technology. The present invention more specifically pertains to a system to optimize the spectromoltial analysis of a given sample by modifying the physical characteristic of a sample spray routed to the burner or plasma torch.

17 Claims, 2 Drawing Sheets

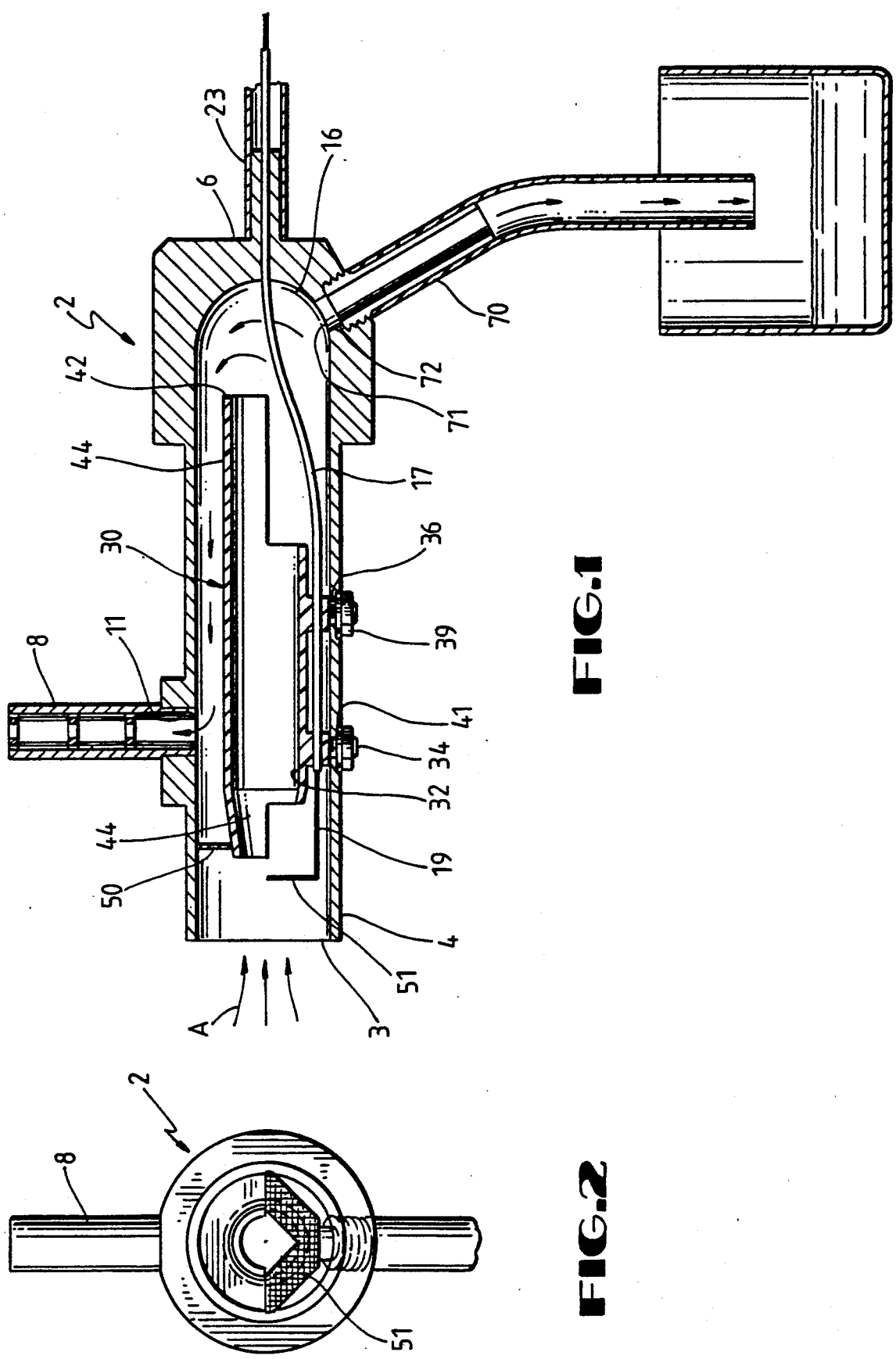

GAS FLOW CHAMBER FOR USE IN ATOMIC ABSORPTION AND PLASMA SPECTROSCOPY

BACKGROUND OF THE INVENTION

1. Field Of The Invention

The present invention pertains generally to atomic absorption and plasma spectrometers, and more particularly, to spectroanalytical systems of the type that sense a special characteristic of a flame by absorption or emission technology. The present invention more specifically pertains to a system to optimize the spectroanalytical analysis of a given sample by modifying the physical characteristics of the sample spray routed to the burner or plasma torch.

2. Description of the Prior Art

In atomic absorption and plasma spectroscopy, measurement of the absorption or emission of radiation at a characteristic resonant spectral line for a particular element yields a measure of the concentration of that element in an original sample. Presently, the most common technique for atomizing an element for purposes of absorption measurement is by introducing a liquid sample containing the element of interest into a gas burner wherein droplets of the sample are vaporized and the elements ultimately atomized so as to form a radiation beam. In plasma emission systems, a liquid sample is nebulized with a plasma gas such as argon, nitrogen, etc. The sample liquid is suspended in microsized droplets which are introduced into the plasma torch wherein the atoms of the liquid are energized from the plasma. Energy emitted by the energized sample is measured by the spectroanalytical system.

In atomic absorption or emission type spectroanalytical systems, the material to be analyzed is introduced into a premix or gas flow chamber by a nebulizing arrangement using a regulated plasma gas or oxidant stream. The plasma gas or oxidant stream is ideally introduced into the gas flow chamber as a fine uniform spray of minute droplets, which droplets are entrained with a combustible fuel or plasma gas and flow through the gas flow chamber into a burner or plasma torch. Upon combustion, the combustible fuel energizes the material to be analyzed for purposes of analysis. In plasma units, the plasma torch energizes the material. An example of a nebulizer arrangement is seen in U.S. Pat. No. 4,220,413.

A nebulizer generally employs a Venturi-type restriction which passes rapidly-moving plasma or gas past an opening, thereby drawing a portion of a liquid sample into the gas stream thereby effecting an atomizing of the liquid. The liquid is aspirated by the Venturi effect caused by the rapidly moving current of gas. In an absorption system, sample laden gas or oxidant then passes into the gas flow or premix chamber, where it is mixed with additional oxidant from an auxiliary inlet and a fuel such as acetylene. The mixture is then introduced into the burner head where it is ignited. Oxidants and fuels are not introduced in plasma systems. Instead, in such systems, the sample laden gas is introduced directly into the plasma torch via a screen type nebulizer or the like.

The sensitivity of an absorption measurement is dependent on a number of factors. In an absorption system, one such factor is the flame condition of the burner—i.e. the leanness or richness of the fuel oxidant mixture. Also, the sensitivity of the measurement usually requires optimization of the setting of the nebulizer which varies the amount of liquid sample aspirated to the burner or plasma torch. Because of the nature of the mechanism for aspirating more or less of the sample, namely varying the flow of oxidant or plasma gas through the venturi-type restriction, there is the obvious side effect on the flame condition or torch which has a direct effect on the sensitivity of the measurement.

In an attempt to achieve a consistent flame or plasma condition, a number of premix or gas flow chambers have been developed. The most common design comprises a first tube horizontally disposed in a larger second tube so as to define a ring-like annulus therebetween. The smaller tube is situated in fluid communication with a nebulizer arrangement at one end and is of a length sufficient to allow a flow space between the remote end of the smaller tube and the larger tube. A burner head or plasma torch is coupled to the larger tube via a passageway disposed in the upper portion of the tube. Sample laden gas introduced into the smaller tube "paints" the inside of the smaller tube and the end of the larger tube, whereupon the sample laden gas then doubles on itself wherein a portion of the combination is moved into the passageway leading to the plasma torch or burner. Due to this characteristic flow path, this type of spray chamber is commonly called a "double pass" spray chamber.

Double pass and similar spray chambers present a number of disadvantages. The design of the double pass gas flow system was motivated by a desire to substantially reduce the introduction of large sample droplets into a burner (or plasma torch in the case of plasma spectroscopy). Therefore, such designs require that a significant surface area of the spray chamber be "painted" by the mist of a liquid sample preliminary to the introduction of the sample into the plasma torch or burner. In this connection, a conventional embodiment of the double pass chamber typically compels spray droplets to travel some nine inches prior to introduction into the burner or ICP plasma torch.

As a result of such designs, however, a relatively low concentration of a given sample solution is actually introduced into the burner or torch. The result of this low concentration flow is the accumulation of solid deposits in the passageway (injector tube) leading to an ICP torch (or burner in the case of atomic spectrometers). This deposition of solid particles is particularly pronounced in plasma spectroscopy, where the ICP torch operates at temperatures in the order of 8000° K. When a low concentration of droplets enter the injector tube (such as in the case in the double pass system), the sample droplets are prone to rapid evaporation. Such evaporation results in the deposition of salts in this tube. These salts must be periodically removed from the injector tube to allow for continual and reliable burner operation. In the case of conventional double pass systems, for example, these salts must be physically removed after every hour of operation where liquid samples having a high salt content are employed.

Aside from the inconvenience compelled by the necessary maintenance of injector tubes, the presence of salts is also undesirable from the standpoint of increasing the coefficient of variation for sample replication. Further, the continual deposition of salts in an injector tube also reduces long term instrument stability.

Other disadvantages of prior art spray chambers include the uneven distribution of sample spray droplets inside the burner or torch. Uneven spray distribution is brought about as a result of large droplets. This problem is especially pronounced when measuring small concentrations of a sample of interest. A large sample droplet, when conveyed to the torch or flame, can result in erratic analyses. The overall result of uneven spray distribution is a loss of instrument sensitivity.

SUMMARY OF THE INVENTION

The present invention addresses the aforementioned and other disadvantages of prior art gas flow chambers by providing an improved spray mixing system compatible with conventional spectroanalytical apparatus. Use of the present system enables a concentrated sample dispersion to be directed to a torch or burner while substantially eliminating the passage of undesired large droplets. The present design also enables a technician monitoring the spectroanalytical instrument to optimize sample gas flow characteristics so as to achieve consistent, replicable analysis using a variety of nebulizers and/or monochromators.

Structurally, the present invention comprises a body provided with a horizontally disposed cylindrical bore therethrough, where said body is coupled to a nebulizer about one end so as to establish flow communication therebetween. A burner or torch outlet is formed in the upper portion of the bore so as to allow flow communication between the torch or burner and the sample concentration introduced into the bore by the nebulizer. A cylindrical inner spray tube is preferably disposed in the bore in such a fashion as to define a uniform, ring-shaped annulus between the exterior of the spray tube and the bore.

The inner spray tube is preferably truncated at both ends so as to define a pair of overhanging-lips. The end of the inner spray tube proximate the nebulizer is provided with a series of gas flow baffles. A first solid baffle is formed between the bore and the top portion of the gas flow tube so as to prevent fluid flow from the nebulizer over the top of the flow tube. The second baffle preferably comprises a "V" shaped screen of a fine mesh. This baffle is axially moveable relative to the proximal end or inlet of the inner spray tube so as to enable the flow characteristics of the sample mixture to be optimized or "tuned".

The present invention has a number of advantages of the prior art. One advantage is improvement in the sensitivity of the spectroanalyzer brought about as a result of an increase in the uniformity of the spray sample. This improvement is attributable in large part to the ability to optimize the individual spray sample directed to the burner or torch.

Other advantages include improved precision and long term stability of the spectroanalyzer. These advantages are accomplished by a reduction in the number of large droplets which are conveyed to the torch or burner. The presence of large droplets causes erratic pulses in the torch or burner, whereby analytical precision is lost. In the present design, large droplets are intercepted by the adjustable baffle, or are directed to the end of the bore where they are subsequently removed from the system.

In the case of plasma spectroanalysis, a third advantage lies in an increased concentration of uniform, microsized droplets in the plasma gas introduced to the ICP torch. The higher concentrations reduce or prevent the formation of salts in the injector tube. The absence of such salts thereby helps to prevent the torch from plugging.

BRIEF DESCRIPTION OF THE DRAWINGS

FIG. 1 illustrates a side, cross-sectional view of one embodiment of the spray mix chamber.

FIG. 2 illustrates an end view of the embodiment illustrated in FIG. 1.

DESCRIPTION OF THE PREFERRED EMBODIMENT

Figure 3:
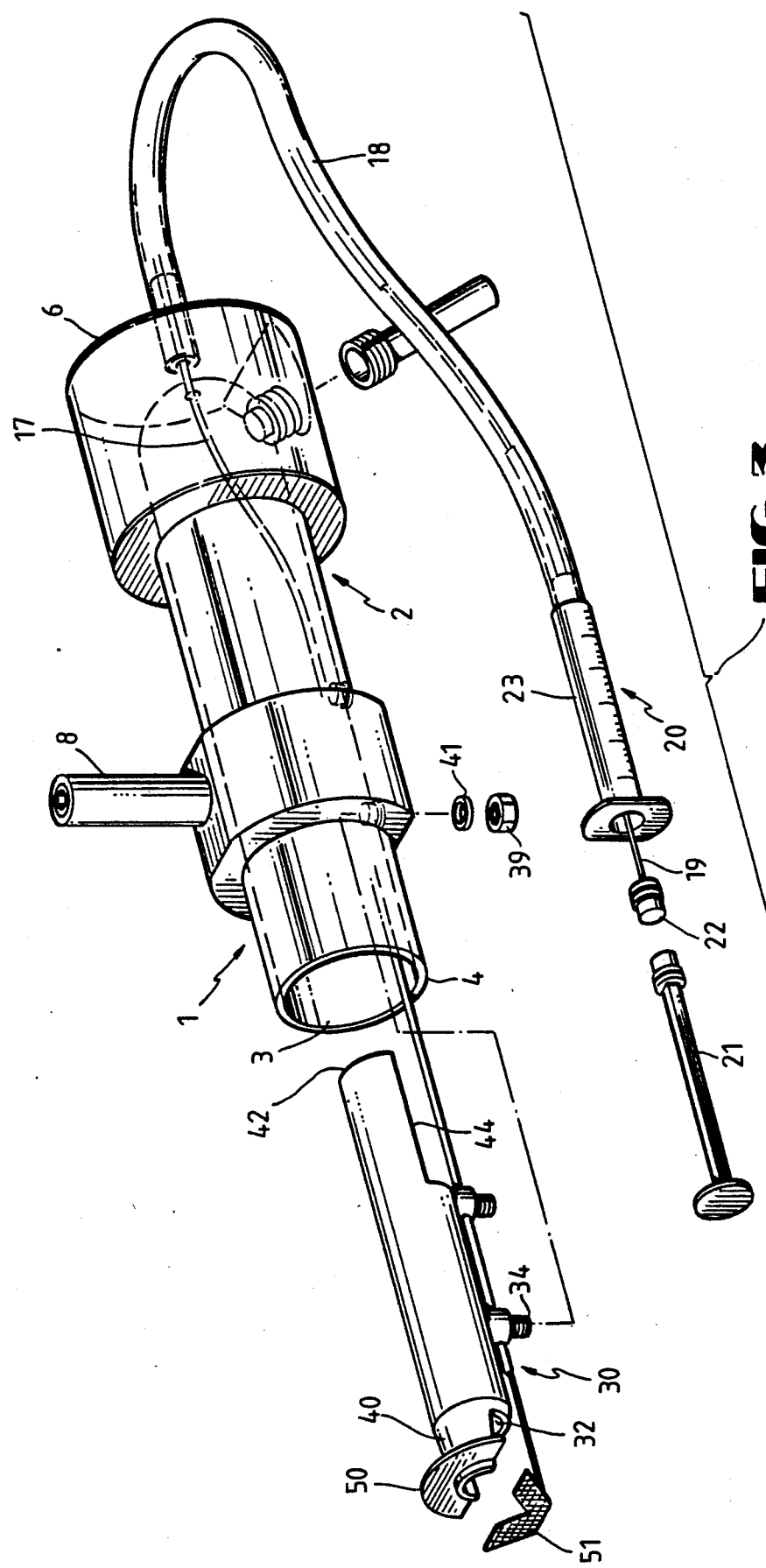
FIG. 3 illustrates a perspective view of the embodiment illustrated in FIG. 1.

FIG. 1 illustrates a body 2 in which is formed a horizontally disposed, cylindrical flow bore 3. Bore 3 has an open end 4 and a rounded, closed end 16. Body 2 is adapted to exist in fluid communication downstream from a conventional nebulizer or the like (not shown), such that a sample laden oxidant or plasma gas stream may be introduced through the open end 4 of bore 3 as shown by arrows "A". Body 2 also exists in fluid communication with a burner or ICP torch (not shown) through an injector tube 8 which is coupled to body 2 via a vertically oriented bore 11. Body 2 is preferably formed of Teflon or other similar material which, in the case of atomic absorption instruments, is preferably coated with stainless steel. Bore 3 is preferably provided with an aperture 71 and a drainage bore 72 in body 2, said bore being coupled to a drainage tube 70. To enable drainage of bore 3 through drainage tube 70, body 2 may be disposed slightly off the horizontal when in an operating condition.

Referring to FIGS. 1-3, flow bore 3 is adapted to receive an inner spray tube 30. Tube 30 is preferably generally cylindrical in shape and defines an inner, cylindrical bore 32 therethrough. Spray tube 30 is preferably also formed from Teflon or other similar material. Spray tube 30 is preferably rigidly coupled to body 2, so as to prevent movement or displacement during the introduction of fluid flow by a nebulizer therethrough open end 4. Other configuration of spray tube 30 are also envisioned in accordance with the spirit of the present invention.

Spray tube 30 includes a first proximal end 40 and a distal end 42 relative to the inlet end of body 2. Spray tube 30 is adapted to be disposed in said bore 3 such that the proximal end 40 of tube 30 corresponds to the open end 4 of bore 3. In such a fashion, the proximal end 40 of spray tube 30 is directed upstream and the axis of tube 30 is generally parallel to fluid flow.

In the illustrated embodiment, spray tube 30 may be provided with threaded protrusions or legs 34 receivable in corresponding apertures 36 disposed in the bottom of body 2 (when viewed in a horizontal orientation) and secured via fasteners 39. To prevent the leakage of fluid through said apertures, a seal washer or O ring 41 may be provided. The purpose of protrusions or legs 34 is to elevate inner spray tube 30 to a position in bore 3 so as to generally define an elongated, toroidal or doughnut shaped annulus therebetween. (See FIG. 2). Preferably, this annulus or flow path is equally dimensioned thereabout. It is envisioned, however, that it may be desirable in some occasions to modify the relative position of spray tube 30 in bore 3, as for example, to restrict the upper and/or lower flow path (when viewed in end section), or to alter the relative heights of the ends of tube 30.

In alternate embodiments (not shown) spray tube 30 may be provided with alignment vanes fixed about its exterior so as to help prevent lateral movement of tube 30 in bore 3. In a preferred embodiment, such vanes may be slidably received in corresponding slots formed in bore 3. In such an embodiment, the possibility of fluid leakage through apertures 36 formed in body is eliminated, since the protrusion or legs would not be needed. Still other means for securing and centering spray tube 30 in the bore are envisioned in accordance with the spirit of the invention and will be obvious to one skilled in the art.

In the preferred embodiment of the invention illustrated in FIGS. 1-3, proximal 40 and distal 42 ends of spray tube 30 are partially truncated so as to define an overhanging lip 44 about each end. Preferably, lips 44 are formed about the top 180° of the spray tube 30 when tube 30 is positioned in its normal, horizontally disposed operating condition. Restated, spray tube 30 is preferably truncated at each end by a plane passing through the optical horizon of tube 30 when viewed in end section as illustrated in FIG. 2. Similar structural modifications of inner tube 30 are also envisioned in accordance with the spirit of the present invention. In this connection, the relative length of lips 44 may be varied with respect to each other. Alternatively, lips 44 may extend circumferentially over a greater or lesser degree range of tube 30 with reference to the optical horizon.

The spray chamber 1 of the present invention is designed to increase or maximize the concentration of fine, particulated liquid which is introduced to the burner or torch via injector tube 8. At the same time, it is desirable that the spray chamber 1 eliminate or substantially reduce the movement of larger solution droplets passing into the burner or ICP torch. To accomplish both of these objectives, inner spray tube 30 is designed so as to increase or maximize the passage of a fine solution mist into the area defined within bore 3 above inner tube 30 which is located injector tube 8. Controlled fluid flow is also accomplished via a baffle arrangement, a preferred embodiment of which is illustrated in the FIGS. 1-3. As illustrated, a first baffle 50 is partially disposed in the annulus formed between the upper proximal end 40 of spray tube 30 and bore 3. This may be accomplished by forming baffle 50 as a separate piece or by forming baffle 50 as an integral portion of body 2 or spray tube 30. In a preferred embodiment, baffle 50 extends over the upper 180° of spray tube 30 when viewed from the optical horizon. (See FIG. 2). In such a fashion, direct fluid flow over the top portion of inner member 30 as defined by lip 44 is reduced or substantially eliminated.

A second baffle 51 is also coupled to the proximal or upstream end of spray tube 30. In a preferred embodiment, second baffle 51 in an end and view as illustrated in FIG. 2, generally describes a "V" shape. Preferably the two arms of baffle 51 describe an angle relative to each other of about 60°. Baffle 51 is preferably formed of a 60 mesh Teflon, although other materials and mesh sizes are contemplated within the spirit of the present invention. The "V" shape in baffle 51 allows the nebulized stream to separate into a "directed nebulizer stream" and a "nondirected nebulizer stream". The directed nebulizer stream is allowed to pass through the "V" in baffle 51. Due to gravity, the random droplets leaving the nebulizer form sample droplets which exit the nebulizer in a nondirected nebulizer stream. Baffle 51 intercepts this nondirected nebulizer stream.

Spray tube 30 is also designed to impinge the flow and concentration of particulated liquid introduced to injection tube 8. The truncation of spray tube 30 at proximal end 40 causes turbulence in the nebulized spray. At this proximal end 40, small microsized droplets are allowed to continue to injector tube 8. Large droplets are directed to fixed baffle 50, along spray tube 30, or to baffle 51. The presence of baffles 50 and 51, and spray tube 30 serve to prevent large droplets from reaching injector tube 8. The truncation 42 of the distal end of spray tube 30 allows the remaining microsized droplets to escape and add to the sample laden gas reaching injector tube 8. Large droplets are trapped by inner spray tube 30 at distal end 42 or collide with the distal end of bore 3.

Flow characteristics of various liquid solutions run through different nebulizer arrangements tend to vary. Similarly, the flow dynamics of the solution laden gas also vary. Therefore, the structural configuration for the gas flow chamber is ideally variable in order to allow the optimum liquid product to be introduced into the burner or ICP torch. In the present invention, this optimization or "tuning" is provided by the second, "V" shaped baffle 51. Second baffle 51 is axially movable relative to the proximal end 40 of spray tube 30. In the preferred embodiment illustrated in FIGS. 1 and 3, the relative position of baffle 51 is adjusted via a semirigid control wire 19. In such a fashion, baffle 51 may be moved into close proximity with inner member 30 or may alternately be moved upstream toward the nebulizer.

The axial movement of baffle 51 allows for a variation in the turbulence of a droplet laden gas passing through and around spray tube 30. When baffle 51 is moved to a position substantially flush with the proximal end 40 of table 30, fluid flow is concentrated through the open middle portion of the "V" such as to concentrate fluid flow through tube 30. In such a fashion, flow of large droplets moved through tube 30 will impact the rounded, closed end 16 of bore 3, condense and subsequently flow through drain 72 and tube 70. Large droplets impacting upper baffle 50 will likewise condense and subsequently be moved to the rear of bore 3 where they may be removed as condensate. Large drops impacting baffle 51 will be separated into smaller constituent particles. The movement of baffle 51 allows the turbulence of the "directed nebulizer stream" to be controlled by the operator. When emission counts obtained at a burner or torch are greatest along with the lowest coefficient of variation for 3 replicated readings, then baffle 51 is considered to be in an "optimum" position.

As indicated, the axial movement of baffle 51 is effected by control wire 19. Due to the corrosive environment present within bore 3, control wire 19 is prefereably stainless steel in composition, and is slidably disposed in a protective sheath 17 which extends through the back portion of body 2 as shown in FIG. 1. Sheath 17 is preferably made of Teflon, though it is envisioned that other corrosive resistant materials having a low coefficient of friction are also applicable. At the exterior of body 2, the combination sheath 17 and control wire 19 are received into a flexible encapsulating tube 18. Tube 18 is sealingly coupled at one end to the closed end 5 of body 2 and at the other end to a baffle control mechanism 20.

Referring to FIG. 3, baffle control mechanism 20 preferably consists of a conventional syringe type tube 23 attachable to tube 18 at one end and adopted to receive to a plunger 21 at the other end. Syringe tube 23 is adapted to slidably and sealingly receive a stopper 22, which stopper is coupled to control wire 19. When assembled, plunger 21 is situated in tube 23 adjacent stopper 21 such that a vacuum may be drawn therebetween. In such a fashion, the movement of plunger 21 in syringe tube 23 dictates the axial position of stopper 22 and baffle 51.

A prototype of the present invention was tested in association with a Perkin Elmer Plasma II Inductively Coupled Plasma Spectrometer. The Perkin Elmer Spectrometer was fitted with two monochromators, a first monochromator (monochromator "A") with 3600 lines/mm grating and a second monochromator (monochromator "B") with 1800 lines/mm grating. Thus equipped, operation of the Perkin Elmer Spectrometer was interfaced with a Concurrent Model 40 megabyte computer which computed the percentage coefficient of variation on replicated analyses for each monochromator.

Using the above setup, the following studies were conducted to measure sensitivity, precision and long-term instrument stability.

A. ICP Sensitivity

Background Equivalency Concentration (BEC) is one method to determine the sensitivity of a spectrometer for any element. In this connection, the BEC allows an evaluation of the sensitivity of the spectrometer resultant from the introduction into the torch of higher concentration of small droplets of sample laden gas.

For purposes of the test, a solution of 0.05 mg/l manganese was analyzed to determine the BEC utilizing a conventional "double pass" spray chamber with a cross flow and Hildebrand grid nebulizers. This was compared to a test run with the spray/mix chamber of the present invention. ("TAEX"). The results of the test are set forth in Table 1.

| SYSTEM | MONO-CHROMATOR | NEBU-LIZER | BEC mg/l |
|---|---|---|---|
| 1. TAEX | A | Hildebrand Grid | 0.014 |
| *neb. @ 0.67 + 1 ml/l | B | Hildebrand Grid | 0.020 |
| 2. TAEX | A | Cross Flow | 0.014 |
| neb. @ .67 + 1 ml/l | B | Cross Flow | 0.021 |
| 3. Double Pass | A | Cross Flow | 0.031 |
| @ STD Conditions | B | Cross Flow | 0.020 |
| 4. Double-Pass | A | Cross Flow | 0.016 |
| Optimized | B | Cross Flow | 0.024 |

*neb = nebulizer rate + pump rate
@ STD neb rate = 1 ml/min + 1 ml/min

As may be seen by reference to Table 1, the spray/mix chamber of the present invention, labeled "TAEX", reduced the BEC regardless of the type of nebulizer used in the test. The values represented in Table 1 are consistent at the same nebulizer rate 0.67 l/min + 1 ml/min pump rate for the Hildebrand grid and cross flow nebulizers.

B. Stability

The spray/mix chamber of the present invention also serves to enhance the precision and stability of the spectrometer. A test was run analyzing 10 replications of 0.05 mg/l manganese and reporting the percentage of coefficient of variation. The results of a test utilizing the present invention, labeled "TAEX", versus a conventional double pass spray chamber are represented in Table 2.

| SYSTEM | MONO-CHRO-MATORS | NEBU-LIZERS | CO-EFFICIENT OF VARI-ATION |
|---|---|---|---|
| 1. TAEX | A | Hildebrand Grid | 1.88 |
| NEB .60 ml/l + 1 ml/min | B | Hildebrand Grid | 1.59 |
| 2. TAEX | A | Cross Flow | 1.64 |
| NEB .60 ml/l + 1 ml/min | B | Cross Flow | 1.31 |
| 3. Double Pass | A | Cross Flow | 4.25 |
| neb @ .6 ml/l + 1 ml/min | B | Cross Flow | 2.49 |
| 4. Double Pass | A | Cross Flow | 2.78 |
| neb @ Std Cond. | B | Cross Flow | 1.57 |

Evident from Table 2, the gas flow chamber of the present invention illustrates a consistently lower percentage of coefficient of variation regardless of the type of nebulizer or monochromator employed. While the double pass chamber produces some useable data, generally the data is unacceptable due to lack of precision.

C. Long Term Stability

Six sample trays of 54 plant sample solutions were assembled for automated analysis. These samples were analyzed during a time span of twelve hours and forty-nine minutes for nine elements. The results of this test are illustrated in Table 3.

| ELEMENT | CONCEN-TRATION | Percentage Coefficient Variation | | | | | |
|---|---|---|---|---|---|---|---|
| | | 12:42 pm | 15:50 pm | 18:02 | 20:00 | 22:42 | 01:33 |
| P | 30.0 | 1.35 | 0.72 | 1.93 | 0.89 | 1.65 | 1.26 |
| Zn | 2.0 | 1.17 | 0.81 | 1.84 | 0.93 | 1.06 | 1.60 |
| Ca | 200.0 | 0.32 | 0.38 | 0.57 | 1.52 | 1.98 | 0.22 |
| Fe | 5.0 | 0.76 | 1.57 | 1.84 | 0.08 | 1.21 | 1.58 |
| Cu | 1.0 | 1.11 | 0.86 | 0.14 | 2.22 | 0.54 | 0.84 |
| Mn | 3.0 | 1.24 | 0.96 | 1.23 | 0.78 | 0.86 | 0.70 |
| Mg | 100.0 | 1.16 | 0.27 | 0.61 | 0.40 | 1.40 | 0.72 |
| Na | 300.0 | 1.19 | 0.87 | 1.47 | 0.81 | 0.85 | 1.05 |
| K | 337.5 | 0.55 | 0.49 | 1.22 | 0.88 | 0.71 | 0.72 |

Data in Table 3 indicates that the gas flow chamber of the present invention is stable and capable of holding precision below a 2.0% coefficient of variation over long-term automated analysis. Only one reading exceeded the 2.0% CV (Copper @ 2.22% CV). In contrast, conventional double pass chambers require the instrument operator to shut down the system every 54 samples (one hour) in order to remove the salts accumulated in the injection tubes.

What I claim is:

1. A gas flow chamber for use in association with atomic absorption and plasma spectroscopy, comprising:

a body defining a horizontally disposed, cylindrical bore therethrough where one end of said bore is coupled in fluid communication with a means to introduce a mist of large and small droplets of a selected solution into said bore also situated in fluid communication with a burner or plasma torch;

a hollow inner member disposed in said bore such as to define a substantially uniform, ring-shaped annulus, said inner member aligned such that the large droplets introduced into said bore tend to flow through said inner member and the said inner smaller droplets tend to flow in said annulus for ultimate deposition in said burner or torch; and said inner member provided with an axially adjustable baffle means to impede the movement of larger droplets in the annulus defined by said inner member and the bore.

2. The gas flow chamber of claim 1 wherein the body comprises an optical horizon which defines upper and lower sections in said bore, and the moveable baffle is situated in said lower section.

3. The gas flow chamber of claim 2 which further comprises a second, fixed baffle arranged in the upper section of said bore and attached to the inner member.

4. The gas flow chamber of claim 1 or 2 which further comprises means to drain the bottom section of said bore.

5. The gas flow chamber of claim 1 wherein the axially adjustable baffle includes a 60 mesh teflon screen.

6. The gas flow chamber of claim 5 wherein said screen has a frontal surface situated approximately normal to the bore and describes a first and second portion diverging from one another so as to form a "V" shape.

7. A spray mixing chamber for use in a spectroanalytical instrument, comprising:
a body defining a horizontally disposed cylindrical bore arranged in upper and lower sections as divided by a horizontal plane, said bore closed at a first end and defining at least one sample inlet at a second end or outlet passageway in the body adapted to be connected to a torch or burner structure; and
a tubular member concentrically disposed in said bore such as to define an annulus therebetween, said tubular member having a first and second end wherein said first end is proximate the sample inlet, the ends of said tubular member being partially truncated about the horizontal plane so as to define a pair of lips above an optical horizon; the first end of said tubular member provided with a fixed baffle above the lip so as to prevent fluid flow between the tubular portion and the bore, said first end of said tubular member also provided with a second, axially adjustable baffle adapted to prevent the introduction of large droplets into said inlet passageway.

8. The chamber of claim 7 wherein the second baffle comprises a screen.

9. The chamber of claim 8 wherein the screen is composed of 60 mesh teflon.

10. In an apparatus for use in a spectroanalytical instrument comprising a torch or burner structure, a spray mixing chamber for supplying a fuel/oxidant mixture or a plasma gas to said burner or torch structure, and a nebulizer for furnishing said fuel oxidant or plasma gas mixture to said spray mixing chamber where said mixture is comprised of large and small droplets, an improved spray/mixing chamber comprising: a body defining a horizontally disposed bore therethrough, the first end of said bore coupled to said nebulizer so as to allow for fluid communication therebetween, a tubular member concentrically dispose in said bore so as to define an annulus therebetween, at least one end of said tubular member being partially truncated about an optical horizon such as to define a lipped top portion, a first end of said tubular member situated proximate said nebulizer, a first baffle secured between an upper portion of the first end of said tubular member and said bore so as to impede the passage of the fuel oxidant mixture or plasma gas therebetween, and a second baffle member axially movable about the lower portion of said first end of said tubular member so as to prevent the flow of large particles through said annulus.

11. The apparatus of claim 10 wherein the second baffle comprises a teflon screen.

12. The apparatus of claim 11 wherein said screen is V shaped such to allow a substantially, unrestricted flow passage into said tubular member.

13. The apparatus of claim 10 wherein said body includes a drain to remove condensate from said bore.

14. A gas flow chamber for use in association with atomic absorption and gas plasma spectroscopy comprising:
a body defining a horizontally disposed bore having a first closed end, and a second inlet end;
a horizontally disposed tubular member positioned within the bore and defining an annular space therebetween, each end of the tubular member being spaced from its corresponding end of said bore;
an outlet in the body spaced from the inlet end of the bore and penetrating the upper portion of the body into the bore;
the lower portion of each end of the tubular member truncated to form an arcuate section of the tubular member at each upper end of the tubular member;
a solid baffle in said annular space between said outlet and the end of the tubular member corresponding to said inlet end and extending around the upper portion of the tubular member; and
a vertically disposed, porous baffle positioned between said inlet end and the lower, truncated, proximate end portion of the tubular member, said porous baffle configured to fit below the arcuate section of the proximate end portion of the tubular member and to define an annular space with the lower portion of said bore.

15. The chamber of claim 14 which further comprises means to move the porous baffle between the outlet and the end of the tubular member corresponding to said inlet end.

16. The chamber of claim 15 wherein the porous baffle is V-shaped in a plane transverse to the bore.

17. The chamber of claim 14 wherein each end of the tubular member is truncated by a first plane passing through the optical horizon of the tubular member and another plane transverse to the first plane and spaced from such end.

* * * * *